(12) United States Patent
Hublot et al.

(10) Patent No.: US 7,750,169 B2
(45) Date of Patent: Jul. 6, 2010

(54) PROCESS FOR THE PREPARATION OF STIRIPENTOL PARTICLES HAVING A DEFINED PARTICLE SIZE DISTRIBUTION

(75) Inventors: Bernard Hublot, Compiegne (FR); Laurence Berthon-Cedille, Ricquebourg (FR); Marie-Emmanuelle Leguern, Compiegne (FR); Gilles Renaud, Courbevoie (FR)

(73) Assignee: Biocodex, Gentilly (FR)

( * ) Notice: Subject to any disclaimer, the term of this patent is extended or adjusted under 35 U.S.C. 154(b) by 0 days.

(21) Appl. No.: 12/357,621

(22) Filed: Jan. 22, 2009

(65) Prior Publication Data

US 2009/0187034 A1 Jul. 23, 2009

(30) Foreign Application Priority Data

Jan. 23, 2008 (FR) .................................. 08 50413

(51) Int. Cl.
*C07D 317/54* (2006.01)
(52) U.S. Cl. ...................................... 549/445; 549/464
(58) Field of Classification Search ................. 549/464, 549/445
See application file for complete search history.

(56) References Cited

U.S. PATENT DOCUMENTS 3,910,959 A    10/1975   Vallet

*Primary Examiner*—Janet L Andres
*Assistant Examiner*—David E Gallis
(74) *Attorney, Agent, or Firm*—B. Aaron Schulman; Terry L. Wright; Stites & Harbison PLLC

(57) ABSTRACT

The invention relates to a process for the preparation of stiripentol particles having a defined particle size distribution.

11 Claims, No Drawings

PROCESS FOR THE PREPARATION OF STIRIPENTOL PARTICLES HAVING A DEFINED PARTICLE SIZE DISTRIBUTION

FIELD OF THE INVENTION

The present invention relates to a process for the preparation of stiripentol particles having a defined particle size distribution.

BACKGROUND OF THE INVENTION

Stiripentol (STP), also called 4-dimethyl-1-[(3,4-methylenedioxy)-phenyl]-1-penten-3-ol, is the compound of the formula:

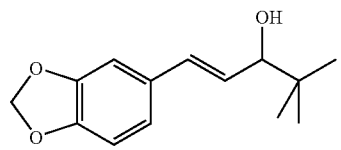

Stiripentol belongs to the family of α-ethylene alcohols which act on the central nervous system. It is capable of treating diseases of the central nervous system and is especially used as a medicament (called Diacomit®) for its anti-epileptic effect, for example in patients suffering from severe myoclonic epilepsy in infancy.

Diacomit® is presented in the form of gelatin capsules containing 250 mg or 500 mg of stiripentol or in the form of granules for a drinkable suspension in a 250 or 500 mg sachet. The particle size distribution of the stiripentol contained in these formulations is such that the diameter of 50% (by number) of the particles (hereinafter denoted $d_{50}$) is less than or equal to 100 μm, especially from 50 to 85 μm, and the diameter of 90% (by number) of the particles (hereinafter denoted $d_{90}$) is less than or equal to 300 μm, especially less than or equal to 250 μm.

These particles can be obtained in accordance with conventional grinding and screening processes in order to produce the defined particle size distribution. However, grinding poses problems because, owing to its relatively low melting point (m.p.=75° C.), stiripentol has a tendency to melt in the course of processing, which results in the particles sticking to each other and therefore in major product losses.

Patent FR 7 343 939 describes the crystallization of stiripentol in ethanol. However, there is no indication as to the particle size distribution of the product obtained. Furthermore, since stiripentol is very soluble in ethanol at ambient temperature, this crystallization process is difficult to transfer to an industrial scale.

A process has now been found which enables stiripentol particles having the desired particle size distribution to be prepared, with good yields, and which can be carried out on an industrial scale. To be more precise, it has been shown that, by effecting recrystallization of stiripentol from an aromatic solvent, it is possible to obtain the desired particle size distribution directly, without subsequent grinding and/or screening steps. In addition, this process enables a product of high purity to be obtained.

SUMMARY OF THE INVENTION

Thus, according to a first aspect, the invention relates to a process for the preparation of stiripentol particles, comprising:
i) the dissolution of the stiripentol in an aromatic solvent;
ii) the crystallization of the stiripentol from the solvent;
iii) the recovery of the stiripentol particles obtained.

Advantageously, the stiripentol particles obtained have the desired particle size distribution, namely a particle size distribution in which:
$d_{50}$ is less than or equal to 100 μm, and is especially from 50 to 85 μm, and
$d_{90}$ is less than or equal to 300 μm, especially less than or equal to 250 μm.

This particle size distribution is measured under wet conditions. By way of example, it can be measured by means of a Malvern Mastersizer 2000 SM apparatus equipped with a Hydro 2000 SM measurement cell, on a sample of 100 mg of stiripentol suspended in 30 ml of water in the presence of a surfactant.

Preferably, the aromatic solvent is selected from meta-, para-, orthoxylene, dichlorobenzene and toluene or a mixture thereof, toluene being very particularly preferred.

Although the concentration of stiripentol in step i) is not a critical factor in the crystallization, it is preferred to operate in the presence of a stiripentol concentration close to the saturation concentration in the solvent considered.

Preferably, in step i), the concentration of stiripentol in the aromatic solvent is from 1 to 2 kg/l (i.e. a concentration of from 4 to 9 mol/l), preferably approximately 1 kg/l.

Typically, step i) is carried out by heating the stiripentol at a temperature of from 70° C. to 100° C. until it has completely dissolved preferably under anhydrous conditions, especially under an inert atmosphere.

In order to remove any traces of colouring, products of the same type as celite (or "Clarcel") or activated carbon may be added to the mixture.

According to a preferred variant, after the stiripentol has dissolved and before step ii), any traces of water present in the solution are removed by azeotropic distillation while heating the mixture under reflux. In the presence of slightly acid water, stiripentol may lead to undesirable products which result, in particular, from condensation reactions of the stiripentol with itself.

The process of crystallizing the stiripentol in step ii) can be accelerated in accordance with techniques known to the person skilled in the art, namely cooling the solution, evaporating a portion of the solvent, adding an anti-solvent or seeding the solution with stiripentol crystals. The mixture is usually maintained under agitation throughout the process of crystallization, in order to obtain a homogeneous suspension and a rapid renewal of the mother liquor around each crystallite.

According to a preferred embodiment, the crystallization of the stiripentol is carried out by cooling, typically at a cooling rate of from −0.4 to −1.5° C./min, to a temperature of generally from 0° C. to −10° C. The mixture is usually maintained at this temperature for/over a period of approximately from 1 to 3 hours.

Preferably, the crystallization of the stiripentol is carried out under agitation. The rate of agitation may vary in accordance with the size and the geometry of the reactor and also in accordance with the type of agitating device. It should be noted, however, that the type of agitating device has no influence on the particle size distribution of the stiripentol obtained. Generally, the operation is carried out at a rate of from 75 to 125 rpm.

Finally, the stiripentol crystals form particles which can be isolated in step iii) in accordance with conventional methods, such as filtration or centrifugation.

According to an especially preferred variant, the process according to the invention also comprises a second recrystallization, preferably in the same aromatic solvent as the first recrystallization. To be more precise, the process also comprises a step iv), subsequent to step iii), of repeating steps i) to iii) starting from the stiripentol particles recovered in step iii).

This double recrystallization advantageously enables the reproducibility of the process and the purity of the product to be improved and a homogeneous and colourless powder to be obtained. Moreover, when, in accordance with a preferred embodiment, the recrystallization is carried out in toluene, the amount of residual toluene is less than 500 ppm, that is to say, very markedly lower than the ICH Q3C standard (International Conference of Harmonization) of 890 ppm.

Preferably, the stiripentol particles recovered, especially after the second recrystallization, are washed with the aromatic solvent and then dried under vacuum at a sufficiently high temperature to remove the traces of residual solvent.

DETAILED DESCRIPTION OF THE PREFERRED EMBODIMENTS

Example 1

Preparation of (±)-(E)-4,4-dimethyl-1-[3,4-methylenedioxy)phenyl]-1-penten-3-ol or stiripentol Stiripentol is prepared from (methylenedioxy-3,4-phenyl)-1-dimethyl-4,4-penten-1-on-3 (code no. D305) prepared in accordance with the patent FR 7 206 676.

Four volumes of methanol per mass of ketone D305 are introduced into a reactor. An aqueous solution of potassium borohydride prepared from potassium borohydride (0.12 kg per kg of ketone), water (0.845 liter per kg of ketone) and 2N sodium hydroxide (0.00235 liter per kg of ketone) is then added. The mixture is maintained at a temperature of from 20° to 25° C., with agitation and under nitrogen.

The mixture is agitated overnight at ambient temperature. The reaction mixture is then diluted with 5 liters of water per kg of starting ketone. The pH is subsequently adjusted to a value of from 8.5 to 9 with hydrochloric acid. The product formed is then dried by centrifugation and washed liberally. The product is then dried in an oven ventilated at 60° C. for 24 hours.

First Recrystallization:

The product obtained is then diluted in toluene at a rate of 1 liter of toluene per kg of dry product. The mixture is then heated to from 80° to 90° C. until the stiripentol has dissolved completely. 2 kg of Clarcel and 3 kg of activated carbon are then added. The mixture is then heated to 110° C. under reflux, and any trace of residual water in the product is removed by azeotropic distillation. The mixture is filtered and then cooled to a temperature of −5° C. for one hour. The mixture is then dried by centrifugation.

Second Recrystallization:

The stiripentol obtained at the end of this first recrystallization is then dissolved in an amount of toluene equivalent to that used in the first purification. The mixture is then heated to 110° C. under reflux and filtered in order to remove any solid impurities. The mixture is subsequently cooled to −5° C. as rapidly as possible, with vigorous agitation (100 rpm) and maintained at this temperature for one hour. The product is then dried by centrifugation and washed with approximately 50 liters of toluene.

Drying the Product:

The product is then dried under vacuum at 40° C. for 24 hours (until a constant mass is obtained). In order to homogenize the batches and avoid the presence of any aggregates which may be formed during the drying operation, the product may be passed through a screen having a mesh size of 1.5 mm. The product may be dried again under vacuum in an oven at 50° C. for 24 hours. The product may be passed through a screen having a mesh size of 630 μm and mixed.

Average yield: 85%
Melting point: 75° C.
Average diameter ($d_{50}$): from 50 to 85 μm.
Diameter of 90% of the particles ($d_{90}$)≦250 μm.

What is claimed is:

1. Process for the preparation of stiripentol particles, comprising:
   i) the dissolution of the stiripentol in an aromatic solvent;
   ii) the crystallization of the stiripentol from the solvent by cooling to a temperature of from 0° C. to −10° C.;
   iii) the recovery of the stiripentol particles obtained.

2. Process according to claim 1, wherein the aromatic solvent is selected from meta-, orthoxylene, dichlorobenzene and toluene or a mixture thereof.

3. Process according to claim 2, wherein the aromatic solvent is toluene.

4. Process according to claim 1, wherein, in step i), the concentration of stiripentol in the aromatic solvent is from 1 to 2 kg/l.

5. Process according to claim 1, wherein the dissolution of the stiripentol in the aromatic solvent is carried out by heating the mixture at a temperature of from 70°C. to 100° C.

6. Process according to claim 1, wherein, after dissolving the stiripentol and before step ii), any traces of water present in the solution are removed by azeotropic distillation.

7. Process according to claim 1, wherein the rate of cooling is from −0.4 to −1.5° C./min.

8. Process according to claim 1, wherein the crystallization of the stiripentol is carried out under agitation.

9. Process according to claim 8, wherein the rate of agitation is from 75 to 125 rpm.

10. Process according to claim 1, also comprising a repetition of steps i) to iii) starting from the stiripentol particles obtained in step iii).

11. Process according to claims 1, wherein the stiripentol particles recovered are washed with the aromatic solvent.

* * * * *